(12) United States Patent
Christian

(10) Patent No.: US 12,261,032 B2
(45) Date of Patent: Mar. 25, 2025

(54) LOW-POWER MASS INTERROGATION SYSTEM AND ASSAY FOR DETERMINING VITAMIN D LEVELS

(71) Applicant: Leidoc, Inc., Reston, VA (US)

(72) Inventor: Noah Peter Christian, San Diego, CA (US)

(73) Assignee: Leidos, Inc., Reston, VA (US)

( * ) Notice: Subject to any disclaimer, the term of this patent is extended or adjusted under 35 U.S.C. 154(b) by 0 days.

(21) Appl. No.: 18/607,766

(22) Filed: Mar. 18, 2024

(65) Prior Publication Data

US 2024/0347330 A1    Oct. 17, 2024

Related U.S. Application Data

(62) Division of application No. 17/544,599, filed on Dec. 7, 2021, now Pat. No. 11,967,495, which is a division
(Continued)

(51) Int. Cl.
| | | |
|---|---|---|
| H01J 49/00 | (2006.01) |
| H01J 49/02 | (2006.01) |
| H01J 49/06 | (2006.01) |
| H01J 49/16 | (2006.01) |
| H01J 49/20 | (2006.01) |
(Continued)

(52) U.S. Cl.
CPC .......... *H01J 49/004* (2013.01); *H01J 49/025* (2013.01); *H01J 49/067* (2013.01); *H01J 49/16* (2013.01); *H01J 49/20* (2013.01); *H01J 49/24* (2013.01); *H01J 49/0013* (2013.01); *H01J 49/30* (2013.01)

(58) Field of Classification Search
CPC ........ H01J 49/025; H01J 49/067; H01J 49/20; H01J 49/10; H01J 49/24; G01N 2560/00; G01N 33/82
See application file for complete search history.

(56) References Cited

U.S. PATENT DOCUMENTS

| | | |
|---|---|---|
| 3,423,583 A | 1/1969 | Durand |
| 3,546,450 A | 12/1970 | Burns |
(Continued)

FOREIGN PATENT DOCUMENTS

| | | |
|---|---|---|
| CN | 108872614 A | 11/2018 |
| GB | 1116807 | 6/1968 |
(Continued)

OTHER PUBLICATIONS

Ginde, A. A., et al., "Demographic Differences and Trends of Vitamin D Insufficiency in the U.S. Population, 1988-2004," Arch. Intern. Med., 169:626-632, 2009.
(Continued)

*Primary Examiner* — David E Smith
*Assistant Examiner* — Hsien C Tsai
(74) *Attorney, Agent, or Firm* — Dawn-Marie Bey; Bey & Cotropia PLLC

(57) ABSTRACT

A low power mass spectrometer assembly includes at least an ionization component, an electrostatic analyzer, a lens assembly, a magnet assembly and at least one detector located in a same plane as the entrance to the magnet assembly for detecting the deflected sample ions and/or fragments of sample ions, including ions or ion fragments indicative of the Vitamin D metabolite within the sample.

15 Claims, 9 Drawing Sheets

Related U.S. Application Data of application No. 16/399,441, filed on Apr. 30, 2019, now Pat. No. 11,227,754.

(60) Provisional application No. 62/664,636, filed on Apr. 30, 2018.

(51) Int. Cl.
  *H01J 49/24* (2006.01)
  *H01J 49/30* (2006.01)

(56) References Cited

U.S. PATENT DOCUMENTS

| | | | |
|---|---|---|---|
| 4,473,748 A | 9/1984 | Konagai | |
| 4,785,172 A | 11/1988 | Kubena | |
| 5,166,518 A | 11/1992 | Freedman | |
| 5,317,151 A | 5/1994 | Sinha | |
| 5,481,110 A | 1/1996 | Krishnaswamy | |
| 6,002,130 A | 12/1999 | Kato | |
| 6,180,942 B1 | 1/2001 | Tracy | |
| 6,182,831 B1 * | 2/2001 | Scheidemann | H01J 49/30 250/281 |
| 6,452,167 B1 | 9/2002 | Felter | |
| 7,402,799 B2 | 7/2008 | Freidhoff | |
| 7,649,171 B1 | 1/2010 | Freidhoff | |
| 9,625,477 B2 | 4/2017 | Holmquist | |
| 2006/0011829 A1 | 1/2006 | Scheidemann | |
| 2010/0282966 A1 | 11/2010 | Schneider | |
| 2012/0032075 A1 | 2/2012 | De Chambost | |
| 2012/0205534 A1 | 8/2012 | Hunter | |
| 2013/0344610 A1 | 12/2013 | Cooks | |
| 2014/0097338 A1 | 4/2014 | Eiler | |
| 2014/0309121 A1 | 10/2014 | Francese | |
| 2015/0017022 A1 | 1/2015 | Fomani | |
| 2015/0348770 A1 | 12/2015 | Hoang | |
| 2016/0086781 A1 | 3/2016 | Cooks | |
| 2016/0202276 A1 | 7/2016 | Meunier | |
| 2017/0131247 A1 | 5/2017 | Gazis | |
| 2017/0271138 A1 | 9/2017 | Christian | |
| 2018/0286647 A1 | 10/2018 | Guckenberger | |

FOREIGN PATENT DOCUMENTS

| | | | |
|---|---|---|---|
| GB | 2402808 | 12/2004 | |
| WO | WO-2007077245 A1 * | 7/2007 | H01J 49/004 |

OTHER PUBLICATIONS

Kennel, et al., "Vitamin D Deficiency in Adults: When to Test and How to Treat," Mayo Clin. Proc., 85(8): 752-758, Aug. 2010.
Volmer, D. A., et al., "Analysis of Vitamin D Metabolic Markers by Mass Spectrometry: Current Techniques, Limitations of the "Gold Standard" Method, and. Anticipated Future Directions," Mass Spectrom. Rev., 34; 2-23, Jan.-Feb. 2015.
Jones, et al., "Vitamin D Metabolite Profiling Using Liquid Chromatography-Tandem Mass Spectrometry (LC-MS/MS)," The Journal of Steroid Biochemistry and Molecular Biology, vol. 164, pp. 110-114, Nov. 2016.
Janetto, et al., "Liquid Chromatography Tandem Mass Spectrometry," Clinical Laboratory News, Jul. 1, 2015, https://www.aacc.org/publications/cln/articles/2015/july/liquid-chromato . . . .
Farrell, et al., "State-of-the-Art Vitamin D Assays: A Comparison of Automated Immunoassays With Liquid Chromatography-Tandem Mass Spectrometry Methods," Clinical Chemistry, vol. 58, Issue 3, Mar. 2012.
Castro, M. D. L,, et al., "Determination of T"amin D3 Metabolites: State-of-the-Art and Trends," I Pharr. Biomed, Anal., 20: 1-17,1999.
Wallace, A. M., et al., "Measurement of 25-Hydroxyvitamin D in the Clinical Laboratory: Current Procedures, Performance Characteristics and Limitations," Steroids, 75(7): 477-488, 2010.
Carter, G. D., et al., "Measurement of Vitamin D Metabolites an International Perspective on Methodology and Clinical Interpretation," J. Steroid Biochem. Mol. Biol., 467-471, 2004.
Yulin Qi, et al., "Rapid Quantification of 25-Hydroxyvitamin D3 in Human Serum by Matrix-Assisted Laser Desorption/Ionization Mass Spectrometry," J. Am. Soc. Mass Spectrom., 2018, DOI: 10.1007/s13361-018-1956-4, 7 pp.
J. J. Amsden, et a., "Proof of Concept Coded Aperture Miniature Mass Spectrometer Using a Cycloidal Sector Mass Analyzer, a Carbon Nanotube (CNT) Field Emission Electron Ionization Source, and an Array Detector," J. Am. Soc. Mass Spectrom., 29, 360-372 (2018).
Wang, et al., "Microscale Gas Chromatography With Microsensor Array Detection: Challenges and Prospects," Eurosensors Proceedings, 1, 633, 2017.
Lin, et al., "A Zone-Heated Gas Chromatographic Microcolum: Energy Efficiency," Sensors and Actuators B: Chemical, Jan. 1, 2018, vol. 254, pp. 561-572.
Van den Ouweland, J. M., et al., "Vitamin D and Metabolites Measurement by Tandem Mass Spectrometry," Rev. Endocr, Metab. Disord., 2013, 14(2): 159-184.
International Search Report and Written Opinion for PCT App. No. PCT/US19/29991, dated Nov. 5, 2019, 15 pp.
Hadjar, et al., "Preliminary Demonstration of an IonCCD™ as an Alternative Pixelatec Anode for Direct MCP Readout in a Compact MS-Based Detector," Journal of the American Society for Mass Spectrometry, vol. 23, pp. 418-424, 2012.
Barnes, J. H., Hieftje, G. M., "Recent Advances in Detector-Array Technology for Mass Spectrometry," Int, J. Mass Spectrom., 238, pp. 33-46 (2004).
Schilling, G. D., et al., "Detection of Positive and Negative Ions From a Flowing Atmospheric Pressure Afterglow Using a Mattauch-Herzog Mass Spectrograph Equipped With a Faraday-Strip Array Detector," J. Am. Soc. Mass Spectrom., 21, pp. 97-103, 2010.
Solyom, D. A., Hieftje, G. M., "Simultaneous or Scanning Data Acquisition? A Theoretical Comparison Relevant to Inductively Coupled Plasma Sector-Field Mass Spectrometers," J. Am. Soc. Mass Spectrom., 14, Issue 3, pp. 227-235, 2003.
J. P. Hauschild, et al., "Mass Spectra Measured by a Fully Integrated MEMS Mass Spectrometer," International Journal of Mass Spectrometry, 264, pp. 53-60, 2007.
"Focus on Field-Portable and Miniature Mass Spectrometers," Presentations From the 12th Sanibel Conference on Mass Spectrometry, J. Am. Soc. Mass Spectrom., 12, pp. 617-618, 2001.
Mo Yang, et al., "Development of a Palm Portable Mass Spectrometer," J. Am. Soc. Mass Spectrom., 19, pp. 1442-1448, 2008.
J. Mitchell Wells, et al., "Implementation of DART and DESI Ionization on a Fieldable Mass Spectrometer," J. Am. Soc. Mass Spectrom., 19, pp. 1419-1424, 2008.
Jorge Andres Diaz, et al., "Test of a Miniature Double-Focusing Mass Spectrometer for Real-Time Plasma Monitoring," Trends in Analytical Chemistry, vol. 21, No. 8, pp. 515-525, 2002.
Guangming Huang, et al., "Direct Detection of Benzene, Toluene, and Ethylbenzene at Trace Levels in Ambient Air by Atmospheric Pressure Chemical Ionization Using a Handheld Mass Spectrometer," J. Am. Soc. Mass Spectrom., 21, pp. 132-135, 2010.
Jesse A. Contreras, et al., "Hand-Portable Gas Chromatograph-Toroidal Ion Tap Mass Spectrometer (GC-TMS) for Detection of Hazardous Compounds," J. Am. Soc. Mass Spectrom., 19, pp. 1425-1434, 2008.
Li Ding, et al., "A Simulation Study of the Digital Ion Trap Mass Spectrometer," International Journal of Mass Spectrometry, 221, pp. 117-138, 2002.
Jorge Andres Diaz, et al., Integration Test of a Miniature ExB Mass Spectrometer With a Gas Chromatograph for Development of a Low-Cost, Portable, Chemical-Detection System, Trends in Analytical Chemistry, vol. 23, No. 4, pp. 314-321, 2004.
Timothy P. Griffin, et al., "Three-Dimensional Concentration Mapping of Gases Using a Portable Mass Spectrometer System," J. Am. Soc. Mass Spectrom., 19, pp. 1411-1418, 2008.
Peter T. Palmer, et al., "Mass Spectrometry in the U.S. Space Program: Past, Present, and Future," J. Am. Soc. Mass Spectrom., 12, pp. 656-675, 2001.

(56) References Cited

OTHER PUBLICATIONS

File History for U.S. Appl. No. 15/462,339, filed Mar. 17, 2017.
File History for U.S. Appl. No. 17/032,207, filed Sep. 25, 2020.
Hadjar, O., Johnson, G., Laskin, J. et al. IonCCD™ for Direct Position-Sensitive Charged-Particle Detection: from Electrons and keV Ions to Hyperthermal Biomolecular Ions. J. Am. Soc. Mass Spectrom. 22, 612-623 (2011). https://doi.org/10.1007/s13361-010-0067-7.
Gregory D. Schilling, "Detection of Positive and Negative Ions From a Flowing Atmospheric Pressure Afterglow Using a Mattauch-Herzog Mass Spectrograph Equipped With a Faraday-Strip Array Detector," J. Am. Soc. Mass Spectrom., 21, pp. 97-103, 2010.
David A. Solyom, et al., "Simultaneous or Scanning Data Acquisition? A Theoretical Comparison Relevant to Inductively Coupled Plasma Sector-Field Mass Spectrometers," J. Am. Soc. Mass Spectrom., 14, pp. 227-235, 2003.
Hadjar, O., et al., "IonCCD™ for Direct Position-Sensitive Charged-Particle Detection: from Electrons and keV ions to Hyperthermal Biomolecular Ions," J. Am. Soc. Mass Spectrom. 22, 612-623 (2011), https://doi.org/10.1007/s13361-010-0067-7.
Castro, M. D. L., et al., "Determination of Vitamin $D_3$ Metabolites: State-of-the-Art and Trends," J. Pharm. Biomed. Anal., 20: 1-17, 1999.

\* cited by examiner

LOW-POWER MASS INTERROGATION SYSTEM AND ASSAY FOR DETERMINING VITAMIN D LEVELS

CROSS REFERENCE TO RELATED APPLICATIONS

The present application is a divisional of U.S. patent application Ser. No. 17/544,599 entitled "AN IMPROVED LOW-POWER MASS INTERROGATION SYSTEM AND ASSAY FOR DETERMINING VITAMIN D LEVELS" filed Dec. 7, 2021, which is a divisional of U.S. patent application Ser. No. 16/399,441, entitled "LOW POWER MASS INTERROGATION SYSTEM AND ASSAY FOR DETERMINING VITAMIN D LEVELS," filed Apr. 30, 2019, which claims the benefit of priority to U.S. Provisional Patent Application No. 62/664,636, entitled "ASSAY FOR DETERMINING VITAMIN D LEVELS," filed Apr. 30, 2018, both of which are incorporated herein by reference in its entirety.

The present application incorporates by reference U.S. patent application Ser. No. 15/462,339 entitled LOW POWER MASS ANALYZER AND SYSTEM INTEGRATING SAME FOR CHEMICAL ANALYSIS, now U.S. Pat. No. 10,872,755.

GOVERNMENT FUNDING STATEMENT

Embodiments disclosed herein may have been conceived or first actually reduced to practice in performance of work under the following Government funding vehicle: AFRL Contract No. FA8650-17-C-9103. As a result, the Government may have certain rights to those embodiments.

TECHNICAL FIELD

The present embodiments are directed to a compact mass spectrometer for the detection and identification of gases, chemical threats, compounds, and biological molecules such as metabolites and small biological molecules, e.g., D-complex vitamins.

BACKGROUND

J. J. Thomson invented the first mass spectrometer in 1913, in 1932 Joseph Mattauch and Richard Herzog invented the double-focusing mass spectrograph, and in 1940 Alfred Nier made a single-focusing mass spectrometer using a 60-degree magnetic sector. Mass spectrographs have existed in variants to the Mattauch-Herzog and Nier-Johnson geometries, but there has been little to no development direct to making a small, compact, low-power arrayed instrument.

The increasing use of improvised explosives, the ever-expanding contraband threat matrix, and the complications that interferents and obscurants pose to detecting these materials has created a need for improved threat detection in the field. Current detectors that use ion mobility spectrometry (IMS) suffer from limited resolution, inevitably leading to increased false alarms as the complexity of samples increases. Large mass spectrometers are gold-standard detectors for explosives and narcotics in the laboratory. There has been considerable effort to reduce these instruments to a handheld system, but there are still unresolved challenges.

Detection time can be limited, because typical designs for portable devices function as a mass filter, capable of measuring only one mass at a time. These systems have a single channel detector and require sweeping through all masses over time. In this process, transient species may be missed. IMS systems are limited due to the need to pulse ions and then measure ion arrival times, and similarly cannot detect all ions simultaneously in a dispersive manner. Some threats tend to form positive ions and others negative ions. This requires switching polarities in the IMS or MS system, further limiting potential sensitivity and throughput. In analyzers, such as time-of-flight instruments, high voltage is usually generated by converting direct current (DC) to an alternating current (AC) voltage, sending it through a voltage multiplier or step-up transformer, and then rectifying the AC voltage to generate DC. This results in corresponding efficiencies as low as 10%.

Further, radio frequency (RF) generation is required for many mass-to-charge traps and filters, such as rectilinear or curvilinear ion traps, quadrupole mass filters, differential mobility spectrometers, and ion funnels. Generally, the capacitance of the quadrupole or trap can lead to small theoretical power consumption values, though in practice the switching electronics play a dominant role in the power consumption of the system.

A significant challenge to a small MS or IMS is the associated size, weight, power, and durability (shock and vibration) limitations associated with the required vacuum system. Most IMS detectors have a sample flow into the inlet and a countercurrent flow in the ion mobility drift cell. These require pumps that have issues with off-gassing (potentially limiting cleardown times), and significant power consumption. Mass spectrometers require even more elaborate pumping systems and rely on higher power (and typically lower durability) pumping systems to achieve their high-vacuum requirements. These factors limit the use of conventional MS for portable explosive trace detectors in handheld environments, e.g., airport security and the like.

Accordingly, high power consumption remains a limitation to development of an effective handheld mass spectrometry device or a small footprint device that may be incorporated into a portable modular system. There remains a need in the art for a reduced footprint, reduced power mass spectrometer.

In the field of biologic molecule identification and detection, Vitamin D deficiency has been linked to reduced immune function, decreased bone health resulting in bone and back pain, fatigue, headaches, depression, hair loss and even increased cancer risks. Further, Vitamin D deficiency is very common. The Centers for Disease Control and Prevention has reported that the percentage of adults achieving vitamin D sufficiency as defined by 25(OH)D of at least 30 ng/mL (to convert to nmol/L, multiply by 2.496) has declined from about 60% in 1988-1994 to approximately 30% in 2001-2004 in whites and from about 10% to approximately 5% in African Americans during this same time. See Ginde A A, et. Al., Demographic differences and trends of vitamin D insufficiency in the US population, 1988-2004. Arch Intern Med. 2009; 169:626-632 and Kennel et al., Vitamin D Deficiency in Adults: When to Test and How to Treat, Mayo Clin Proc. 2010 August; 85(8): 752-758. And, of late, more people have been found to be severely deficient in vitamin D [25(OH)D<10 ng/mL].

But even given the prevalence of D vitamin deficiency, universal screening has not been accepted since known testing methods require sophisticated and costly laboratory equipment in order to perform analyses; which further requires an expert user in a laboratory facility in order to properly determine Vitamin D levels in healthy and diseased persons. Accordingly, many individuals often go untested and undiagnosed.

Currently, the two primary methods are used for Vitamin D determinations are High performance liquid chromatography (HPLC) of prepared samples and immunoassay methods. And the "gold standard" methodology, liquid chromatography tandem mass spectrometry ((HP)LC-MS/MS, hereafter LC-MS/MS), follows HPLC separation with further analysis, i.e., mass spectrometry (MS). LC-MS/MS is described in numerous references including: Volmer, D. A. et al., Analysis of vitamin D metabolic markers by mass spectrometry: current techniques, limitations of the "gold standard" method, and anticipated future directions, Mass Spectrum Rev. 2015 January-February; 34: 2-23; Jones et al., Vitamin D metabolite profiling using liquid chromatography-tandem mass spectrometry (LC-MS/MS), The Journal of Steroid Biochemistry and Molecular Biology, Volume 164, November 2016, Pages 110-114 and Janetto et al., "Liquid Chromatography Tandem Mass Spectrometry," Clinical Laboratory News, Jul. 1, 2015. And in Farrell et al., State-of-the-Art Vitamin D Assays: A Comparison of Automated Immunoassays with Liquid Chromatography-Tandem Mass Spectrometry Methods, Clinical Chemistry, Vol. 58, Issue 3, March 2012, LC-MS/MS based assays were determined to be superior to automated immunoassay determinations when specifically applied to detecting Vitamin D (25-hydroxy vitamin D (25OH-D)). The inaccuracies from matrix effects on immunoassay determinations limit the ability to read immunoassay strips directly, and many approaches such as lateral flow immunoassay do not yield reproducibly quantifiable signal.

But the LC-MS/MS based assays, though superior in results compared to other methods, present other challenges to implementation in a clinical setting for use in detecting small biological molecules, such as D-complex vitamins. A high complexity system, LC-MS/MS requires a high level of technical expertise to develop and validate tests as well as troubleshoot the instruments.

Accordingly, there remains a need in the art for low cost, high sensitivity assays for detecting biological molecules such as metabolites and small biological molecules, e.g., D-complex vitamins.

SUMMARY OF THE EMBODIMENTS

In a first embodiment, a mass spectrometer assembly for performing tandem mass spectrometry, includes: an ionization component for producing sample ions from a sample; an electrostatic analyzer for receiving the sample ions from the ionization component and producing a preferred set of sample ions; a lens assembly for receiving the preferred set of sample ions from the electrostatic analyzer and focusing the preferred sample set of ions; a magnet assembly for receiving the focused preferred sample set of ions at an entrance thereof and deflecting sample ions within the focused preferred sample set of ions using zero power to a first detector located in a same plane as the entrance to the magnet assembly for detecting the deflected sample ions, wherein individual sample ions are deflected to different points along the first detector in accordance with an individual mass thereof, and an ion fragmentation component located in a region of the first detector, wherein the ion fragmentation component fragments one or more individual sample ions received at the first detector into fragments and the fragments are deflected to a second detector located in the plane of the first detector array.

In a second embodiment, a process for performing tandem mass spectrometry, includes: producing, by an ionization component, sample ions from a sample; receiving by an electrostatic analyzer, the sample ions from the ionization component and producing a preferred set of sample ions; receiving by a lens assembly, the preferred set of sample ions from the electrostatic analyzer and focusing the preferred sample set of ions; receiving, at an entrance of a magnet assembly, the focused preferred sample set of ions and deflecting sample ions within the focused preferred sample set of ions using zero power to a first detector located in a same plane as the entrance to the magnet assembly; detecting the deflected sample ions, at a first detector, wherein individual sample ions are deflected to different points along the first detector in accordance with an individual mass thereof, fragmenting, by an ion fragmentation component located in a region of the first detector, one or more individual sample ions received at the region of the first detector into fragments and deflecting the fragments, by the magnet assembly, to a second detector located in the plane of the first detector array; and detecting, by the second detector, the fragments, wherein fragment detection enables identification of individual components within the sample.

BRIEF DESCRIPTION OF THE FIGURES

The following figures are intended to represent exemplary embodiments and should be considered in combination with the detailed description below.

DETAILED DESCRIPTION

Figure 1:
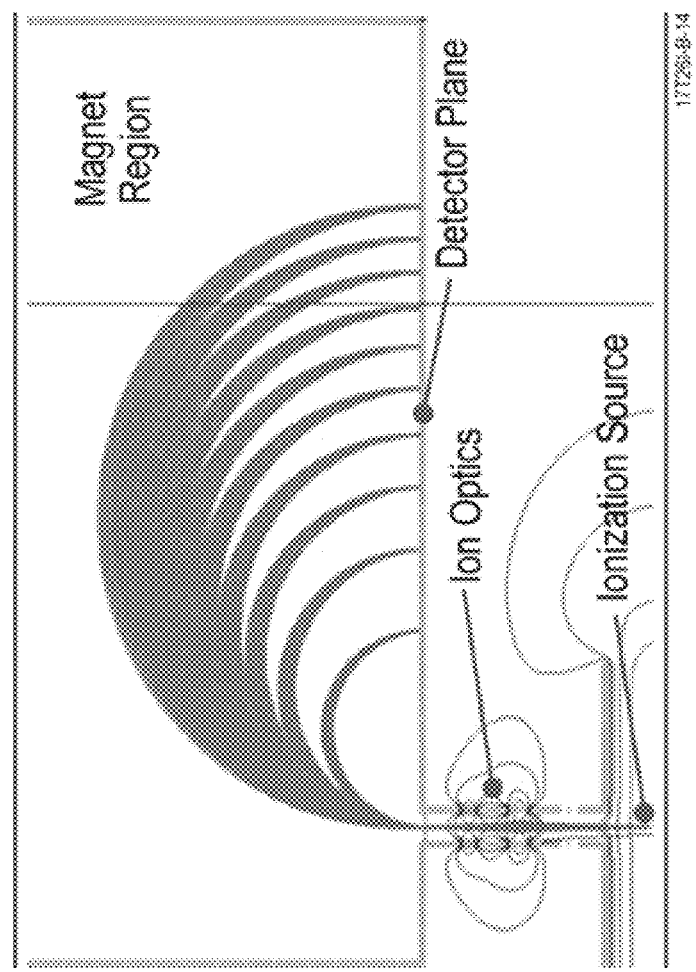
FIG. 1 illustrates an exemplary ion identification system in accordance with one or more embodiments herein.

Referring to FIG. 1, also found in co-owned U.S. patent application Ser. No. 15/462,339, which is incorporated herein by reference in its entirety, the LOMION design is optimized for space, wherein objects in focus at the entrance of the magnetic sector are focused at the detector plane 180 degrees from the entrance. This 180 degree configuration offers greater separation in a minimal space than the prior art Mattauch-Herzog (M-H) design which uses a 90 degree turn and ions are defocused if their trajectories continue. This zero power mass analyzer capitalizes on the fundamental physics principle that ions in motion in a magnetic field will change direction based on their momentum, but the magnetic field will not perform work on the ion. Because there is no work performed on the ion, no energy is consumed. Therefore, mass separation accomplished using a magnetic field (in this case, using a permanent magnet) will not consume any power. This is in contrast to quadrupole mass filters and ion trap mass spectrometers that require the application of radiofrequency (RF) power to separate ions.

Figure 2A:
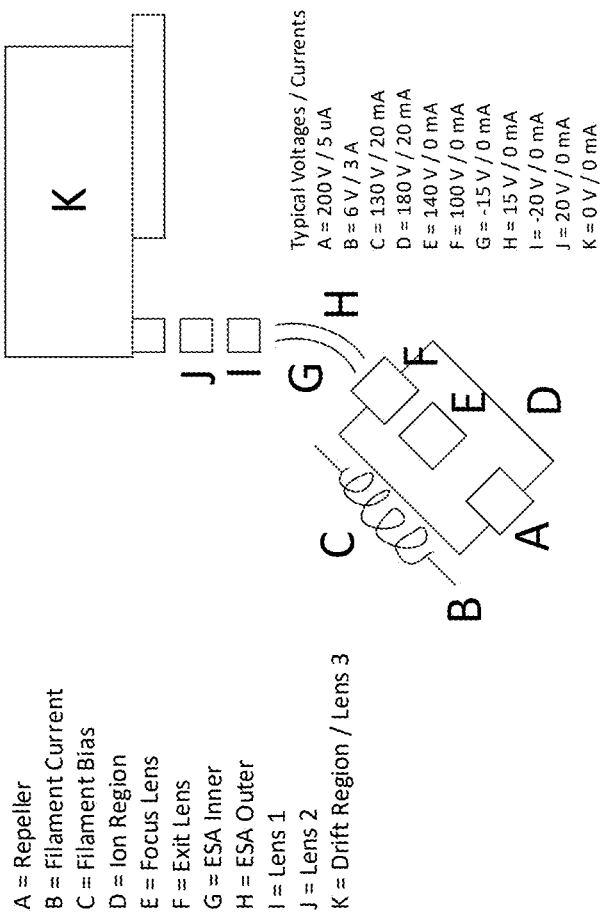
FIGS. 2a and 2b illustrate various aspects of a low-power mass interrogation system (LOMION) system in accordance with one or more embodiments herein.
Figure 2B:
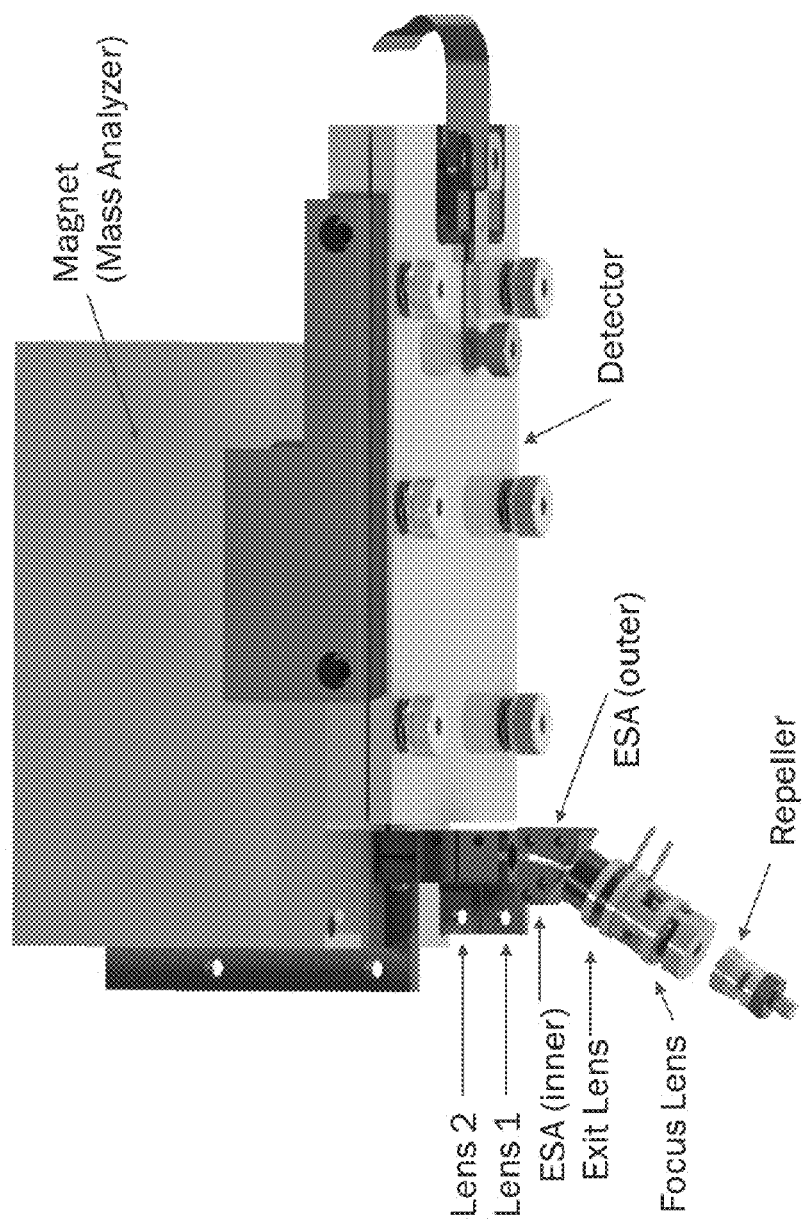

FIGS. 2a and 2b illustrate an exemplary LOMION system in accordance with the embodiments herein, showing the hardware and associated voltage/current specifications. Power supplies were used to provide voltages to the various elements of the system, and we used a consistent naming convention across the program. In accordance with the labeling in FIG. 2a, the ions are formed across the filament (B) with a bias (C) applied to cause electrons to go to the ion region (D) as well as the repeller (A). Positive ions are formed in the ion region (D) and are sent via the repeller (A) to the focus lens (E) and the exit lens (F) prior to the electrostatic analyzer ("ESA") (inner and outer plates G and H respectively). Lens 1 (I) and Lens 2 (J) were used to provide the final focus to the ions as they entered the magnetic sector "drift region" (K) (also referred to as a lens). In a preferred embodiment, a micro D-15 connector may be used for feedthroughs carrying voltage, and a high density connector, such as those available from Samtech, may be used for the ionizer. FIG. 2b references the detector which may be an IonCCD sensor.

In a first exemplary embodiment, the LOMION system may be evacuated by a commercial turbopump, backed by a rough pump of either diaphragm or rotary vane design. In an alternative embodiment, the interstage of the system is exposed to the inlet region as part of a reduced-size vacuum chamber with turbo pump, permitting medium compression ratios for inlet gases and an ultimate vacuum in that region of approximately $10^{-4}$ torr, and a higher vacuum region for the analyzer (portions of the electrostatic lenses as well as the magnet) of approximately $10^{-6}$ torr. One skilled in the art recognizes that the system is capable of operating at higher pressures, with considerations and tradeoffs related to the ionizer.

In an exemplary embodiment, the ionizer used in the ion region/body (D) may be a thermionic source which includes the repeller (A), a filament (including filament current (B) and filament bias (C)), as well as electrostatic elements, i.e., a focus lens (E), and an exit lens (F), wherein the filament may be selected from either a tungsten filament or an yttria coated tungsten filament. But a small and efficient, non-thermionic (filament-free) and non-radioactive ionization source may be used to further reduce the overall power consumption in the system. These alternative ionization sources operate via field emission of electrons and may be selected from e.g., an array of field emitter tips in an array of ring electrodes (field emitter array or FAE) and carbon nanotube (CNT) ionizers. Exemplary ionization sources which may be used with one or more of the embodiments described herein are also described in, e.g., J. J. Amsden et al., "Proof of Concept Coded Aperture Miniature Mass Spectrometer Using a Cycloidal Sector Mass Analyzer, a Carbon Nanotube (CNT) Field Emission Electron Ionization Source, and an Array Detector," J. Am. Soc. Mass Spectrom. 29, 360-372. (2018), the entirety of which is incorporated herein by reference.

After the ionizer, an electrostatic analyzer (ESA) is provided and includes two curved electrodes, inner and outer plates G and H respectively. The ESA eliminates the flow of neutrals and oppositely charged particles from the magnet, as well as providing some energy filtering from the source.

Figure 3B:
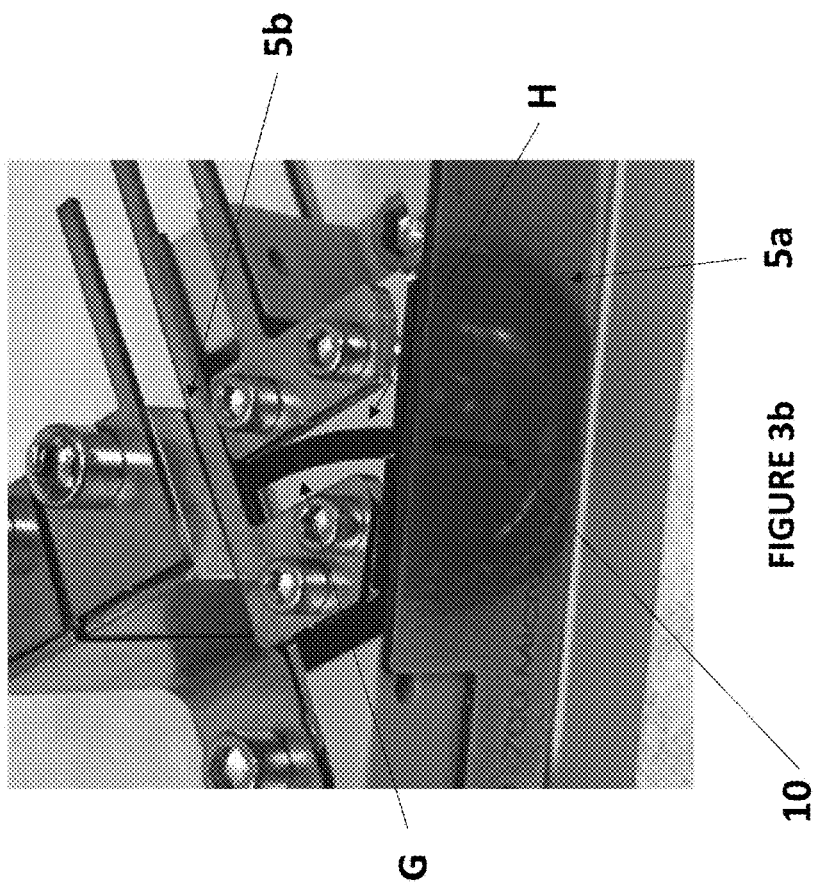
FIGS. 3a and 3b illustrate ion optics features for a low-power mass interrogation system (LOMION) system in accordance with one or more embodiments herein.
Figure 3A:
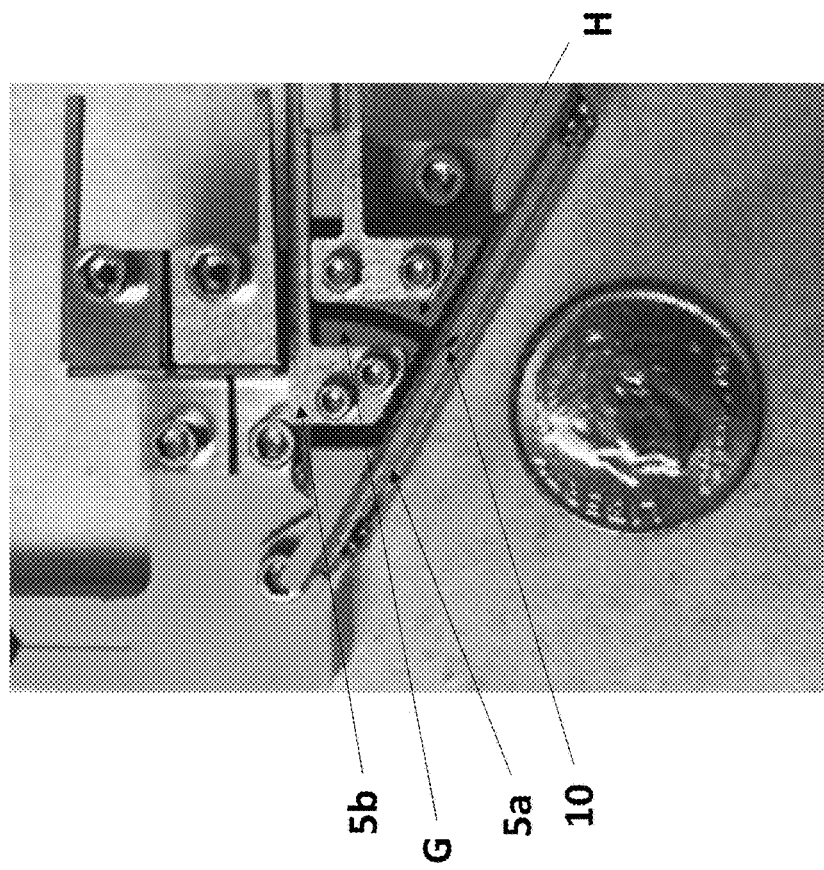
Figure 4B:
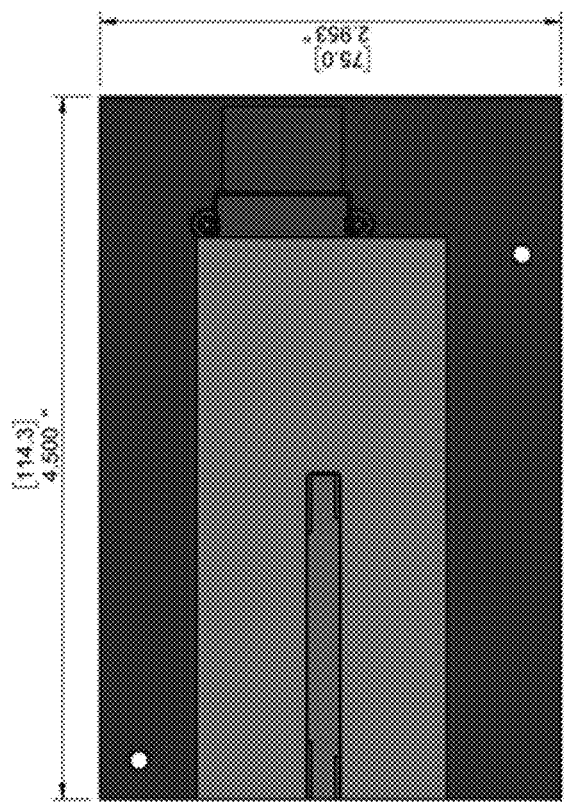
FIG. 4a through 4d illustrate detector array and processing configuration for a low-power mass interrogation system (LOMION) system in accordance with one or more embodiments herein.
Figure 4A:
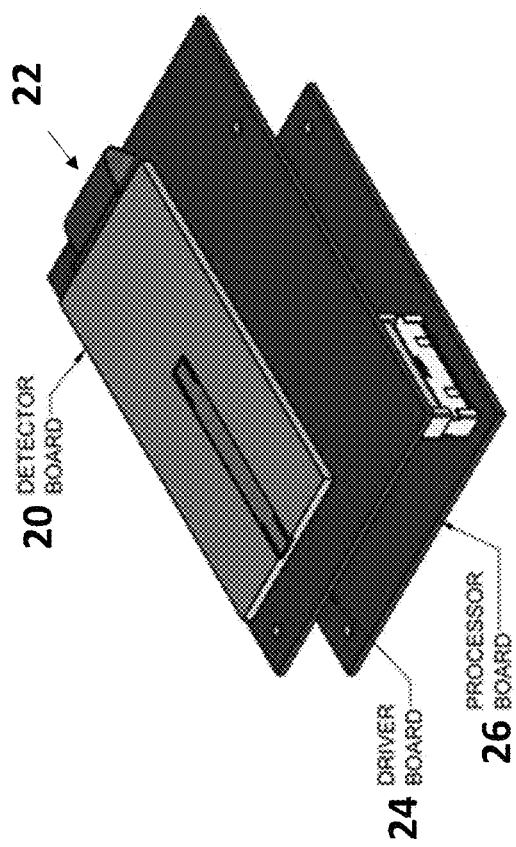
Figure 4D:
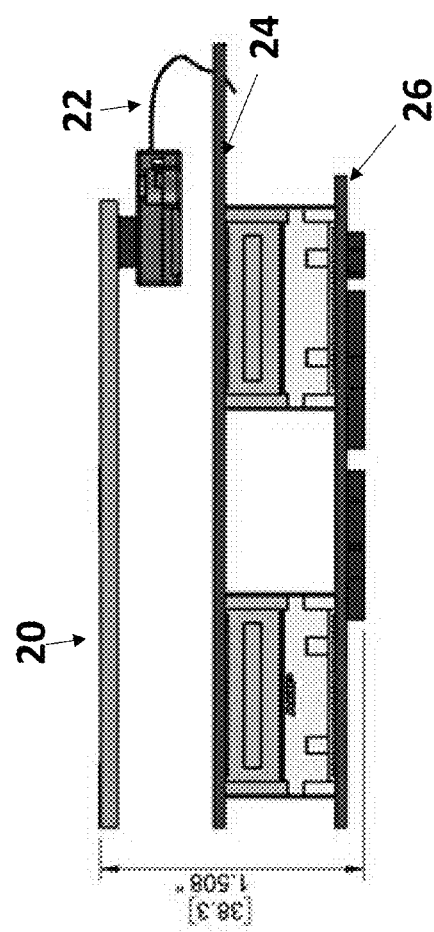
Figure 4C:
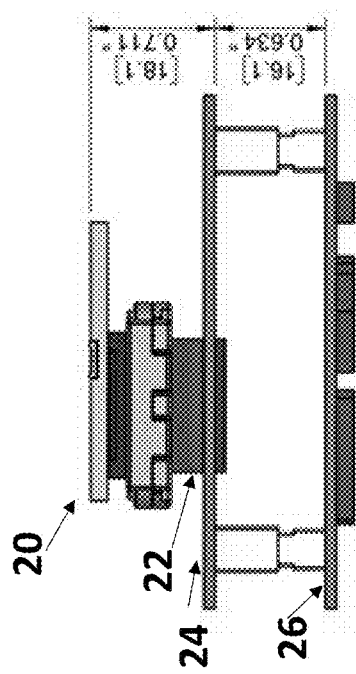

After the ESA, Lens 1 (I) and Lens 2 (J) provide focusing fields to the ions as they enter the magnet (mass analyzer). FIG. 2b also shows the flat exit lens going from the ionizer to the ESA. FIGS. 3a and 3b show the flat entrance plate 5a (with slit 10) and exit plate 5b (with slit not shown) added to the electrostatic analyzer (including inner ESA plate G and outer ESA plate H) to improve performance.

The magnetic sector "drift region" (K) includes a Halbach array Nd:Fe:B (neodymium iron boride; NIB) magnet with a fixed gap of approximately 1 mm and a field strength of approximately 1 Tesla. This produces the separation of ions from the source and electrostatic lenses in a novel arrayed configuration. Ions that are defocused in the magnetic sector "drift region" (K) are refocused at the detector that is placed immediately at the exit of the magnet.

An exemplary detector is a commercial IonCCD detector by OI Analytical. The IonCCD detector works similar to a linear CCD; however instead of detecting photons, it detects and intrinsically integrates charges. There is no charge amplification in the system (via electron multiplier, faraday cup, microchannel plate, etc.). This exemplary detector functions much like a digital camera, and collects all ions at once at a focal plane array. This greatly increases the throughput of the system and allows for passive (no power) ion accumulation, wherein power is only consumed during readout. The efficiency of the IonCCD is optimized to reduce the power consumption during operation. In FIGS. 4a to 4d, dimensions and physical layout views for the detector and the detector readout electronics are shown. The detector board 20 is mounted inside the vacuum chamber and connected via, e.g., a Samtec ribbon cable 22 to the readout electronics, i.e., driver board 24 and processor board 26. The entire footprint is approximately 4.5 inches by 3.0 inches by 1.5 inches, with intermediate dimensions indicated in FIGS. 4b to 4d.

Figure 5B:
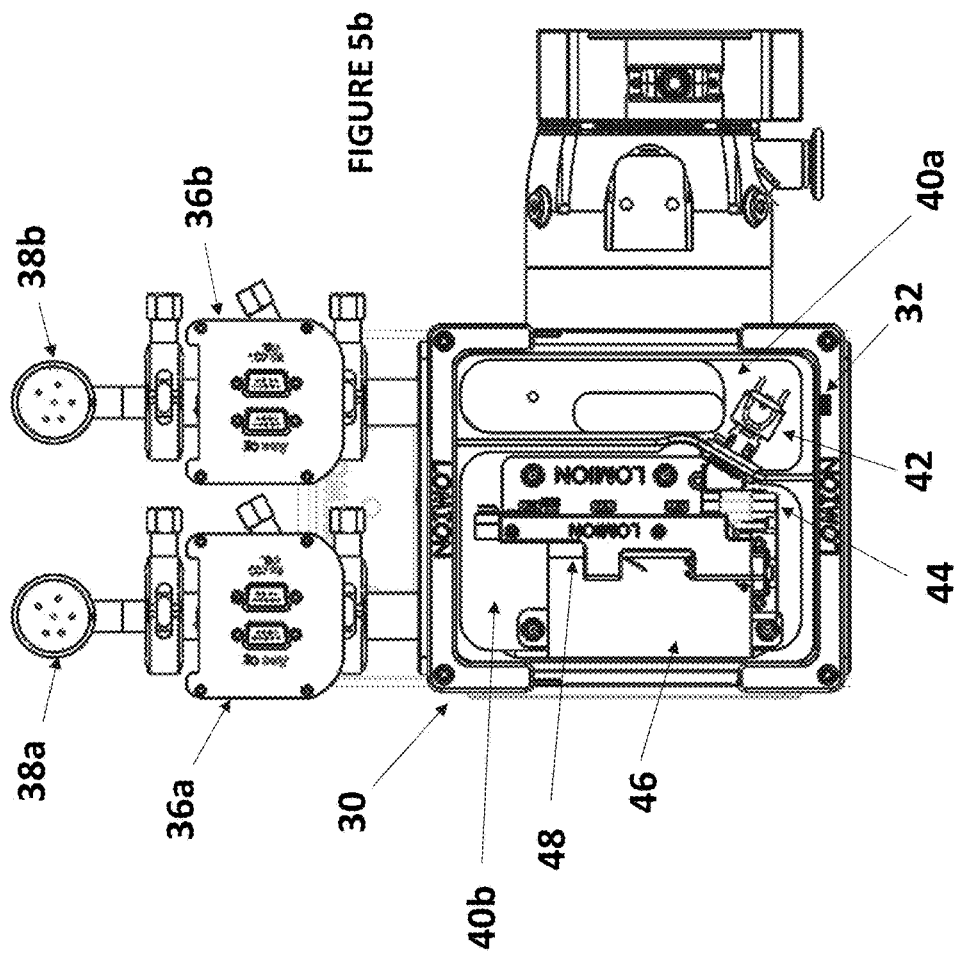
FIGS. 5a and 5b illustrate various components of a stand-alone low-power mass interrogation system (LOMION) system in accordance with one or more embodiments herein.
Figure 5A:
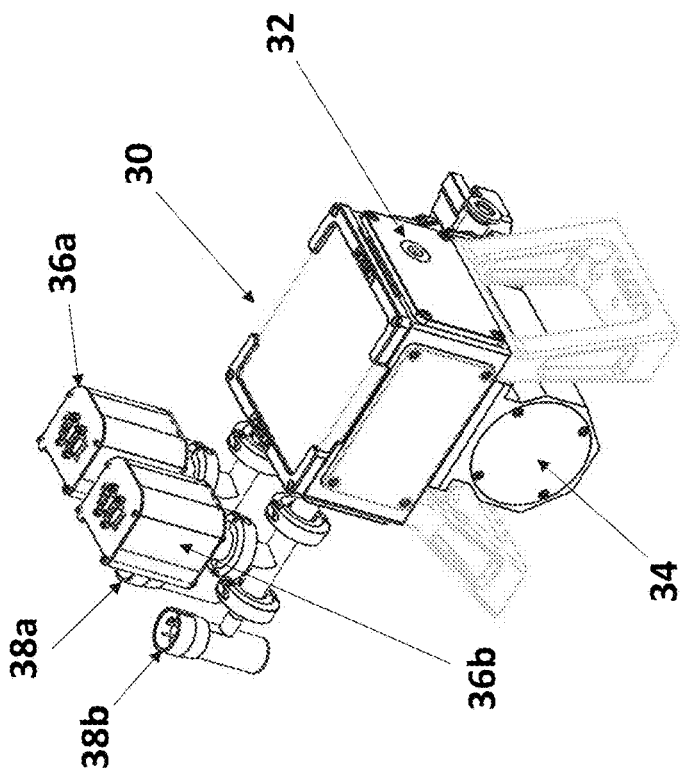

FIGS. 5a and 5b show various views of an exemplary stand-alone LOMION system incorporating the components discussed above. In FIG. 5a, an ion identification vacuum chamber 30 containing two sub-chambers (see FIG. 5b) includes external sample inlet 32, a pump 34, dual ionization gauges 36a, 36b and dual vacuum gauges 38a, 38b. The dual sub-chambers allow for differential vacuum regions, wherein the pump 34 is a turbopump with a main inlet and exposed interstage to support differential pumping. The top view in FIG. 5a shows the internal sub-chambers 40a, 40b, wherein inlet 32 is connected to ionization region sub-chamber 40a which includes ionizer 42. The mass spectrometer chamber 40b houses the ion optics 44, magnet 46 and detector plane 48.

Figure 6:
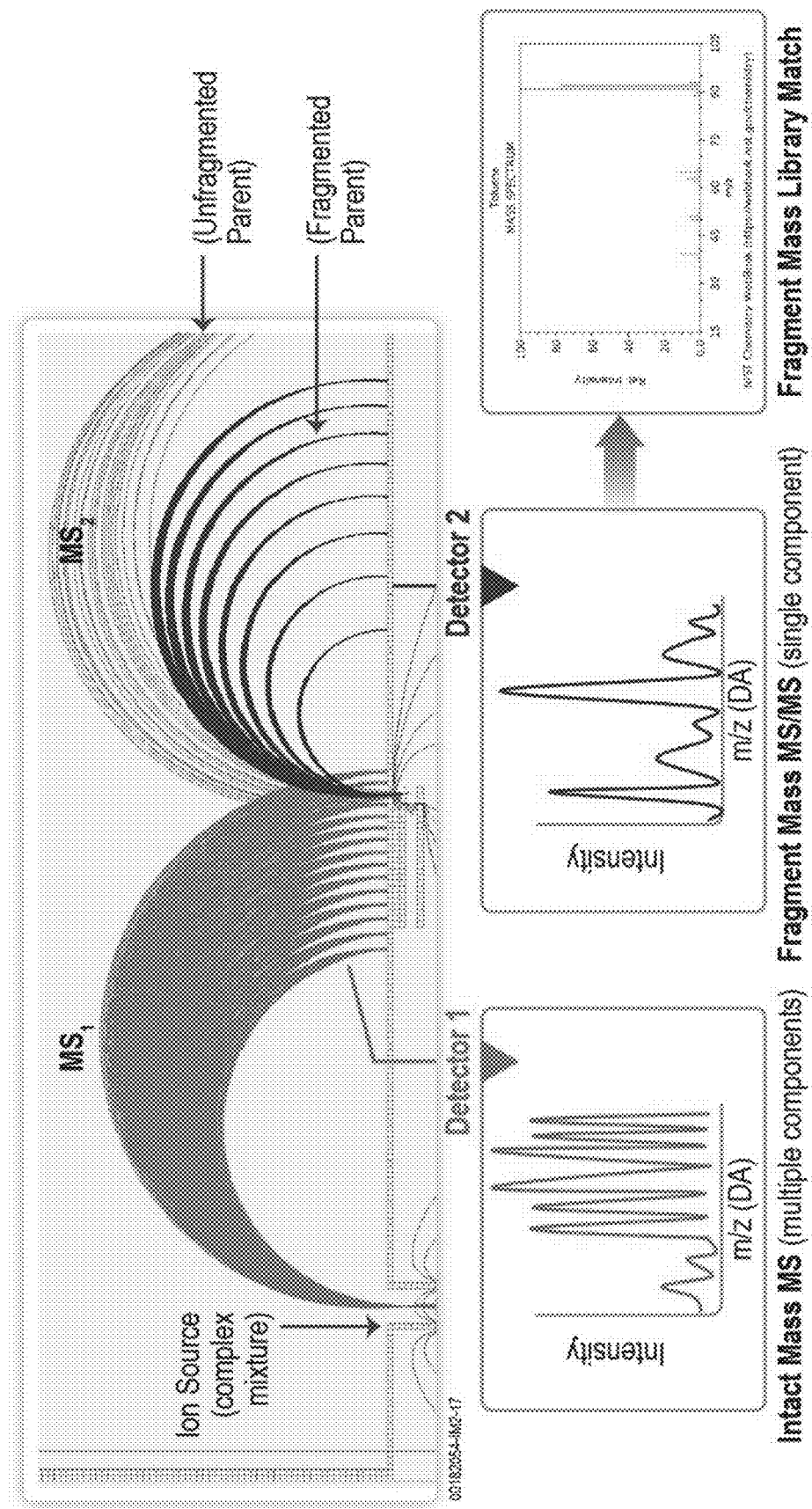
FIG. 6 illustrates an exemplary tandem ion identification system in accordance with one or more embodiments herein.

A second LOMION system, LOMION Plus, in accordance with an alternative embodiment is shown in FIG. 6. The LOMION Plus system will allow for field identification of chemicals in high background levels. The LOMION Plus system expands on the LOMION single 180 degree zero power ion separation turn as part of $MS_1$, to provide for a second 180 degree zero power ion separation turn as part of $MS_2$ to produce and detect ion fragments, thus producing a tandem MS system (i.e., MS/MS system). The ion identifier process in the LOMION Plus system includes a first stage of identification $MS_1$ comprising the ionized sample containing a complex mixture entering magnetic region, ion selection and separation via a first magnetic field and detection of separated ions at a first detector array. Next, in a second stage of identification $MS_2$, certain parent ions are selected, fragmented and redirected, the fragments are sorted via second magnetic field and subsequently detected at a second detector array. Unfragmented parents are not detected The first stage of $MS_1$ is similar to the first phase of LOMION's identifier, but instead of generating fragment masses for each eluting component, it generates intact masses for each chemical species using softer ionization. At the region of the first detector, we add a spatially resolved ion mirror (a reflectron array) with electron bombardment fragmentation. Fragments are sent back through the magnet and follow a second trajectory to separate fragment ions, enabling us to determine structural information for a particular m/z parent ion. The low power MS/MS approach permits true, simultaneous measurement of all parent ions, except for the selected m/z sent to the second MS. This selected ion can be sent to the second detector by adjusting the potential field in front of the detector to be higher than the potential of the ions originally from the ion source. For example, if the ions were accelerated with 100V, 120V on an arrangement of wires in front of the detector is sufficient to deflect them away from the detector and back through the magnet for a second pass. If electrons are sent from a source biased at 30V near this region, they will be accelerated towards the 120V wires but can encounter the ion passing through this region. They act as a 70 eV electron that can induce fragmentation in the parent ion as it encounters the parent. Alternatively, collision induced or surface induced dissociation can be used. After fragmentation, the fragment ions are sent back through the magnet, and all of the fragments formed are resolved on the second detector. Because all parent ions are read at the first detector except for the fragments sent to the second detector, this architecture has unprecedented throughput, operates continuously, and no ions are lost in the analysis process.

The LOMION Plus system rejects background by maintaining a high dynamic range. In a real-time spectrum of a PFTBA (perfluorotributylamine) scan with a very high air background, the air components (oxygen, nitrogen, water) overwhelmed the lower ⅓ of the spectrum, leading to counts in excess of 65,000. The PFTBA components, on the other hand, were as low as 100 counts. This rejection ratio is more than 650:1, which is remarkable for any MS. In comparison, a typical prior art TOF system uses an 8-bit digitizer and typically has a dynamic range of less than 250:1 due to detector saturation and quantization noise, with typical performance around 60:1. An ion trap-even a large trap such as the Thermo-Finnigan LTQ cannot trap more than 100,000 ions; therefore, the ability to see these smaller peaks would be impossible due to the large abundance of water, nitrogen, and oxygen in the sample. It would require a quadrupole or other "lossy" filter to eliminate the lower peaks before filling the trap, or complex tuning to prevent these backgrounds from overwhelming the trap. The LOMION Plus is able to detect phosphonate esters, glycol ethers, and fuel additives; consequently, these interferents should not cause any significant degradation in performance.

The LOMION Plus system operates from 12 Da to 300 Da, which has been sufficient to identify all compounds. One skilled in the art recognizes that higher masses are certainly possible; there are no fundamental physics limitations to expanding this mass range further in either direction. Current hardware permits rapid repositioning of the detector or magnet injection voltage to change the collected mass range. Further, while the preferred implementation collects and identifies gas-phase samples in ambient air, one skilled in the art will appreciate that the system may be adapted to analyze bulk liquids or solids as well as aerosols.

Figure 7:
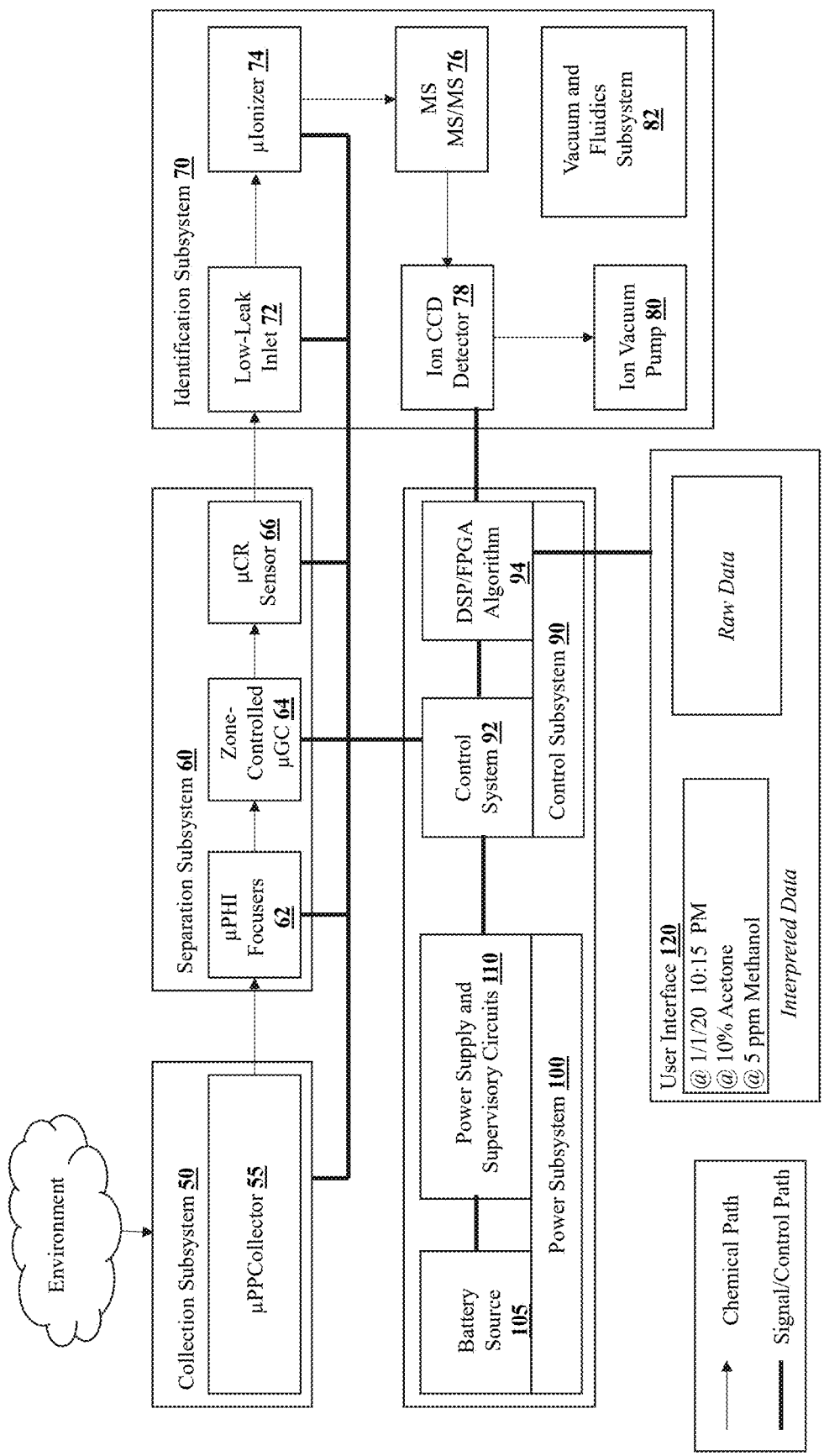
FIG. 7 is a schematic illustrating a components of a low-power mass interrogation system (LOMION) Plus system including a tandem ion identification system of FIG. 6 in accordance with one or more embodiments herein.

The LOMION Plus system may be integrated with one or more additional subsystems in accordance with intended environment and sample focus. FIG. 7 is a schematic showing both pre-identification subsystems one or more of which may be integrated with the LOMION Plus identification system including: a collection subsystem 50, e.g., a micro Passive Preconcentrator ("PP") collector 55, which passively collects sample from the environment onto a microfabricated adsorbent system and a separation subsystem 60 for receiving the collected sample transferred from the collection system. The separation subsystem 60 may include a Preconcentrating Heated Injector ("PHI") 62 focuser system for focused chromatography injections, wherein sample is then eluted at very low flow (<=100 μl/min) across a zone heated microfabricated GC separator 64 and microfabricated chemiresistors ("CR") sensor 66 to a smart, low leak inlet 72 at the entrance to the LOMION Plus identification system 70. Additional subcomponents within the LOMION Plus identification system include a very low thermal mass ionizer region 74 and sample separation under a single or multiple stages of MS 76 as described above, depending on sample complexity and background levels, to the Ion CCD detector 78. The detector readout electronics include the hardware and software 94 for extraction of raw data as well as identified compounds at the user interface 120. A control subsystem 90 is connected to all other components via control system 92, including power subsystem 100 which includes battery source 105 and power supply and supervisory circuits 110.

As discussed in the Background, there are generally two clinical tests for Vitamin D levels in sera: immunoassay and HPLC. These two approaches do not agree in terms of absolute concentrations in sera. It has generally been found that combining HPLC with another readout system such as mass spectrometry, i.e., LC-MS/MS, lends to better concentration measures, and is generally accepted as a viable route to improving performance. But HPLC systems use considerable amounts of buffer, solvent, and solution, and require an expert user to interpret results. The present embodiments utilize parts of immunoassay testing, combined with mass spectrometry realized through an improved low-power mass interrogation system (LOMION) to provide an efficient, low cost, small footprint clinical assay approach to Vitamin D testing. On skilled in the art will recognize that the low power MS systems described and referenced herein may be used for the detection and identification of gases, chemical threats, and compounds not limited to the Vitamin D determinations discussed herein.

The current embodiment reduces the complexity of the gold standard LC-MS/MS based assays by effectively removing the (HP)LC step and combining immunoassay with MS (or MS/MS). The current embodiment uses antibodies tailored to Vitamin-D complex to 'pull down' Vitamin D, i.e., 25(OH)D (including $25(OH)D_3$ and $25(OH)D_2$) from serological samples as a precursor step. This precursor step is not used to quantify Vitamin D levels, rather it is used as a preparative method to sequester Vitamin D from a serological sample volume. There is sufficient antibody to "pull down" all of the Vitamin D without saturating, an important point for quantification. Exemplary immunoassay precursor steps which may be used in the current embodiment find description and support in the following references which are incorporated herein by reference in their entireties: Castro M D L et al. Determination of vitamin $D_3$ metabolites: state-of-the-art and trends. J Pharm Biomed Anal 1999; 20: 1-17; Wallace A M et al. Measurement of 25-hydroxyvitamin D in the clinical laboratory: current procedures, performance characteristics and limitations. Steroids 2010; 75: 477-488; Carter G D et al. Measurement of vitamin D metabolites an international perspective on methodology and clinical interpretation. J Steroid Biochem Mol Biol 2004; 467-471.

This antibody preparative step eliminates the complex machinery and consumables of high performance liquid chromatography (HPLC), which enables point of care/point of use capture of Vitamin D levels in serological fluids.

Next, readout of the Vitamin D levels is produced by denaturing the antibody, consequently releasing the Vitamin D into a buffer solution. The buffer solution does not contain antibody. Antibody can be eliminated by a number of methods including: gravimetrically or centrifugally separating the sample passing through a size exclusion filter; separating an immobilized antibody on a surface from Vitamin D in solution; or changing buffer content to precipitate the antibody from the sample.

Once the Vitamin D is released into buffer, the solution is brought to a mass spectrometer, and the actual amount of Vitamin D is confirmed and quantified. The mass spectrometer is kept very small and low-cost to minimize the overhead and required space for such an analysis. By way of example, the low power mass analyzer described in co-owned U.S. patent application Ser. No. 15/462,339 entitled Low Power Mass Analyzer and System Integrating Same for Chemical Analysis, the entirety of which is incorporated by reference herein, is suitable for detecting the Vitamin D in the buffer.

In a preferred embodiment, the immunoassay precursor step is used to pull down 25(OH)D from a serological sample. The antibody is separated from the 25(OH)D using direct laser desorption and the resulting solution is introduced to a mass spectrometer such as that described in U.S. patent application Ser. No. 15/462,339 and herein. This laser desorption may include a small molecule chemical matrix to assist in the laser desorption of the Vitamin D small molecule as ions into the mass spectrometer.

In an alternative embodiment, an HPLC assay is incorporated with a low power mass spectrometer described in U.S. patent application Ser. No. 15/462,339 and herein as the identifier.

An improved compact low-power mass interrogation system (LOMION) for use with the embodiments discussed above is capable of identification of a wide range of chemicals and biologic molecules using a new architecture for mass separation coupled with efficient ionization and detection. This system enables handheld low-power chemical detection for a large number of target compounds in handheld, fixed-site, and/or leave-behind applications for intelligence, surveillance, reconnaissance (ISR) and biologic molecule detection applications.

The following documents are incorporated herein by reference in their entireties for their teachings: Ginde A A, et. Al., Demographic differences and trends of vitamin D insufficiency in the US population, 1988-2004. Arch Intern Med. 2009; 169:626-632; Kennel et al., Vitamin D Deficiency in Adults: When to Test and How to Treat, Mayo Clin Proc. 2010 August; 85(8): 752-758; Volmer, D. A. et al., Analysis of vitamin D metabolic markers by mass spectrometry: current techniques, limitations of the "gold standard" method, and anticipated future directions, Mass Spectrom Rev. 2015 January-February; 34: 2-23; Jones et al., Vitamin D metabolite profiling using liquid chromatography-tandem mass spectrometry (LC-MS/MS), The Journal of Steroid Biochemistry and Molecular Biology, Volume 164, November 2016, Pages 110-114; Janetto et al., "Liquid Chromatography Tandem Mass Spectrometry," Clinical Laboratory News, Jul. 1, 2015; Farrell et al., State-of-the-Art Vitamin D Assays: A Comparison of Automated Immunoassays with Liquid Chromatography-Tandem Mass Spectrometry Methods, Clinical Chemistry, Vol. 58, Issue 3, March 2012; Castro M D L et al. Determination of vitamin $D_3$ metabolites: state-of-the-art and trends. J Pharm Biomed Anal 1999; 20: 1-17; Wallace A M et al. Measurement of 25-hydroxyvitamin D in the clinical laboratory: current procedures, performance characteristics and limitations. Steroids 2010; 75: 477-488; Carter G D et al. Measurement of vitamin D metabolites an international perspective on methodology and clinical interpretation. J Steroid Biochem Mol Biol 2004; 467-471; Wang et al., Microscale Gas Chromatography with Microsensor Array Detection: Challenges and Prospects, Eurosensors Proceedings, 2017, 1, 633; Lin et al., "A zone-heated gas chromatographic microcolum: Energy efficiency," Sensors and Actuators B: Chemical, 2018 Jan. 1, Vol. 254, pg 561-572; van den Ouweland J M et al., Vitamin D and metabolites measurement by tandem mass spectrometry, Rev Endocr Metab Disord. 2013 June; 14(2):159-84.

One skilled in the relevant art will recognize that there are numerous alternatives to the components discussed herein which are existing in the prior art and which may be substituted in the embodiments to perform the described functions. These are considered to be within the scope of the present embodiments.

The invention claimed is:

1. A mass spectrometer assembly for performing tandem mass spectrometry, comprising:
   an ionization component for producing sample ions from a sample;
   an electrostatic analyzer for receiving the sample ions from the ionization component and producing a preferred set of sample ions;
   a lens assembly for receiving the preferred set of sample ions from the electrostatic analyzer and focusing the preferred sample set of ions;
   a magnet assembly for receiving the focused preferred sample set of ions at an entrance thereof and deflecting sample ions within the focused preferred sample set of ions using zero power to a first detector located in a same plane as the entrance to the magnet assembly for detecting the deflected sample ions, wherein individual sample ions are deflected to different points along the first detector in accordance with an individual mass thereof; and
   an ion fragmentation component located in a region of the first detector, wherein the ion fragmentation component fragments one or more individual sample ions received at the first detector into fragments and the fragments are deflected to a second detector located in the plane of the first detector array.

2. The mass spectrometer of claim 1, wherein the ion fragmentation component comprises a spatially resolved ion mirror with electron bombardment fragmentation.

3. The mass spectrometer assembly of claim 1, wherein a magnet of the magnet assembly is selected to have a field strength of approximately 1 Tesla.

4. The mass spectrometer assembly of claim 2, wherein the magnet is made of Nd:Fe:B.

5. The mass spectrometer assembly of claim 1, wherein the first detector and the second detector are IonCCD detectors.

6. The mass spectrometer assembly of claim 1, further comprising a vacuum chamber housing the ionization component, the electrostatic analyzer, the lens assembly, the magnet assembly, the ion fragmentation component and the first and second detectors.

7. The mass spectrometer assembly of claim 6, further comprising at least one pump connected to the vacuum chamber.

8. The mass spectrometer assembly of claim 6, wherein the vacuum chamber includes first and second chambers to facilitate differential vacuum regions, wherein the ionization component, the electrostatic analyzer and the lens assembly are in a first vacuum region and the magnet assembly and the first and second detectors are in a second vacuum region.

9. The mass spectrometer assembly of claim 1, wherein the ionization component includes a thermionic source.

10. The mass spectrometer assembly of claim 1, wherein the ionization component includes a filament-free and non-radioactive ionization source selected from field emitter array and carbon nanotube (CNT) ionizers.

11. The mass spectrometer assembly of claim 1, wherein the sample is selected from a group consisting of gas, liquid and aerosols.

12. A process for performing tandem mass spectrometry, comprising:
    producing, by an ionization component, sample ions from a sample;
    receiving by an electrostatic analyzer, the sample ions from the ionization component and producing a preferred set of sample ions;
    receiving by a lens assembly, the preferred set of sample ions from the electrostatic analyzer and focusing the preferred sample set of ions;
    receiving, at an entrance of a magnet assembly, the focused preferred sample set of ions and deflecting sample ions within the focused preferred sample set of ions using zero power to a first detector located in a same plane as the entrance to the magnet assembly;
    detecting the deflected sample ions, at a first detector, wherein individual sample ions are deflected to different points along the first detector in accordance with an individual mass thereof;
    fragmenting, by an ion fragmentation component located in a region of the first detector, one or more individual sample ions received at the region of the first detector into fragments and deflecting the fragments, by the magnet assembly, to a second detector located in the plane of the first detector array; and
    detecting, by the second detector, the fragments, wherein fragment detection enables identification of individual components within the sample.

13. The process of claim 12, wherein the ion fragmentation component comprises a spatially resolved ion mirror with electron bombardment fragmentation.

14. The process of claim 12, wherein the first and second detectors enable identification of sample cions having a range of masses from 12 Da to 300 Da.

15. The mass spectrometer assembly of claim 12, wherein the sample is selected from a group consisting of gas, liquid and aerosols.

* * * * *